United States Patent [19]

Zagon et al.

[11] Patent Number: 5,426,112
[45] Date of Patent: Jun. 20, 1995

[54] GROWTH REGULATION AND RELATED APPLICATIONS OF OPIOID ANTAGONISTS

[75] Inventors: Ian S. Zagon, Hummelstown; Patricia J. McLaughlin, Harrisburg, both of Pa.

[73] Assignee: Scully, Scott, Murphy & Presser, P.C., Garden City, N.Y.

[21] Appl. No.: 21,191

[22] Filed: Feb. 23, 1993

Related U.S. Application Data

[60] Division of Ser. No. 740,972, Aug. 6, 1991, Pat. No. 5,266,574, which is a continuation of Ser. No. 900,575, Aug. 26, 1986, abandoned, which is a continuation-in-part of Ser. No. 598,092, Apr. 9, 1984, Pat. No. 4,689,332.

[51] Int. Cl.$^6$ .......................................... A61K 31/41
[52] U.S. Cl. ................................. 514/282; 514/812
[58] Field of Search ............................... 514/282, 812

[56] References Cited

U.S. PATENT DOCUMENTS

| | | | |
|---|---|---|---|
| 4,546,103 | 10/1985 | Huebaner. | |
| 4,600,718 | 7/1986 | Huebaner. | |
| 4,678,779 | 7/1987 | Meyers et al. | |
| 4,689,332 | 8/1987 | McLaughlin et al. | 514/282 |
| 5,266,574 | 11/1993 | Zagon et al. | 54/812 |

OTHER PUBLICATIONS

Amir et al. (1979) "Naltrexone Administration . . . in Rats" *Neuropharmacology* 18(1):905–907.
Zagon et al. (1983) "Naltrexone Modulates Growth in Infant Rats" *Life Sciences* 33:2449-2454.
Chikara et al. (1978) *Chem. Abst.* 88:183495z.
Grandison et al. (1980) *Chem. Abst.* 93:37699f.
Zagon et al. (1984) *Chem. abst.* 100:18090x.
Ilinski et al. (1985) *Chem. Abst.* 103:207085x.

*Primary Examiner*—Herbert J. Lilling
*Attorney, Agent, or Firm*—Scully, Scott, Murphy & Presser

[57] ABSTRACT

A method for regulating the growth processes in a myriad of cells, tissues, organ systems and unicellular and multicellular organisms including plants, animals and man by the administration of effective amounts of the opioid antagonists naloxone, naltrexone, their analogs, metabolites derivatives, and/or mixtures thereof. At the cellular level, the growth processes entail all mitetic events and related processes including cell proliferation, as well as cell migration and cell differentiation, and at the somatic or organismal level, anatomical, behavioral and neurological development, metamorphisis and maturation. Growth regulation can be effected in vivo and/or in vitro.

2 Claims, 8 Drawing Sheets

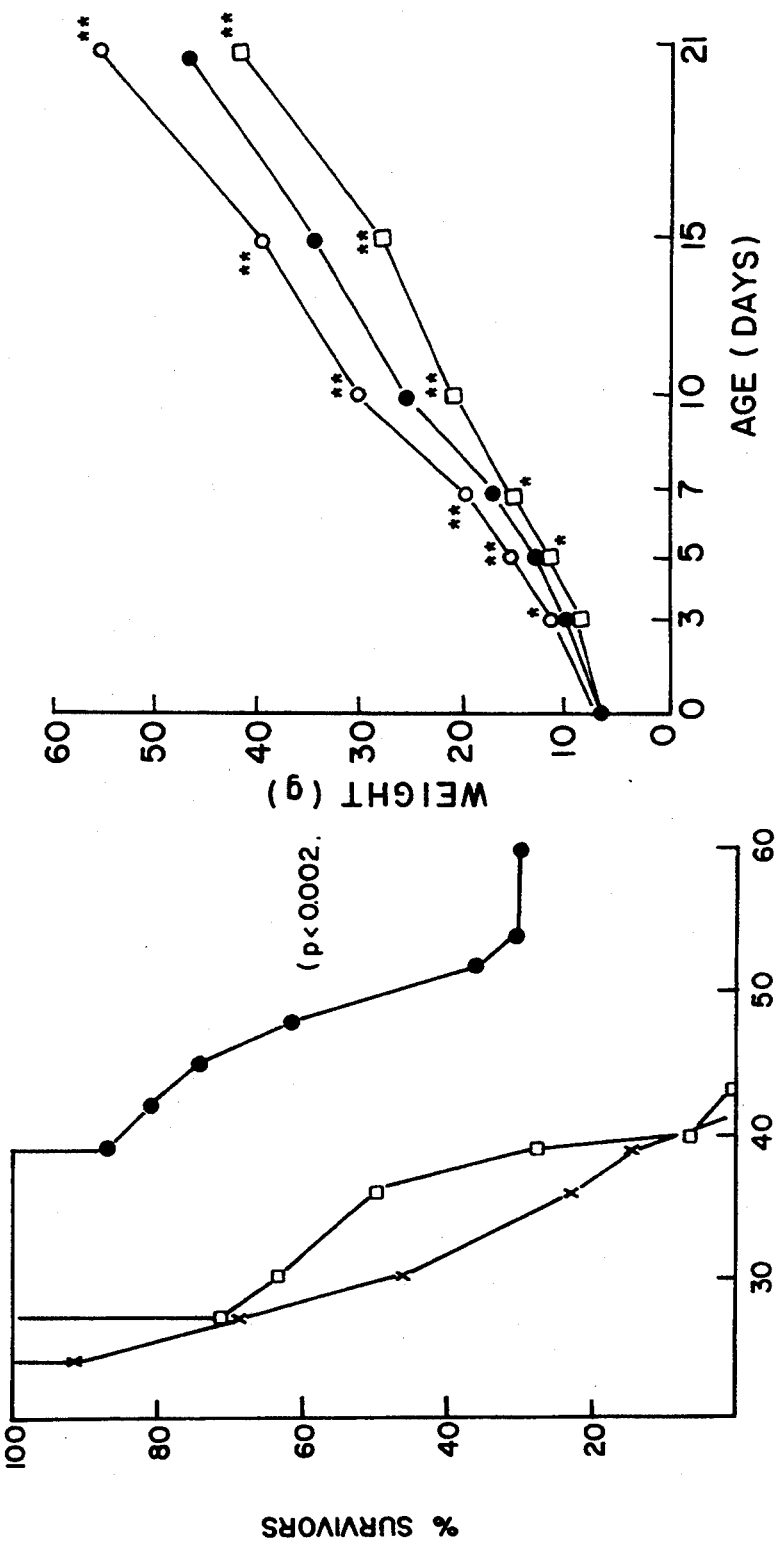

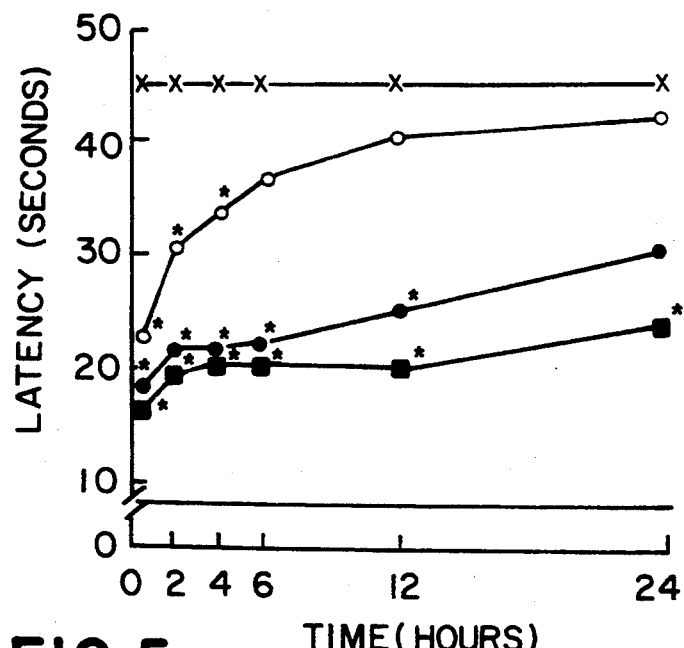
FIG. 5
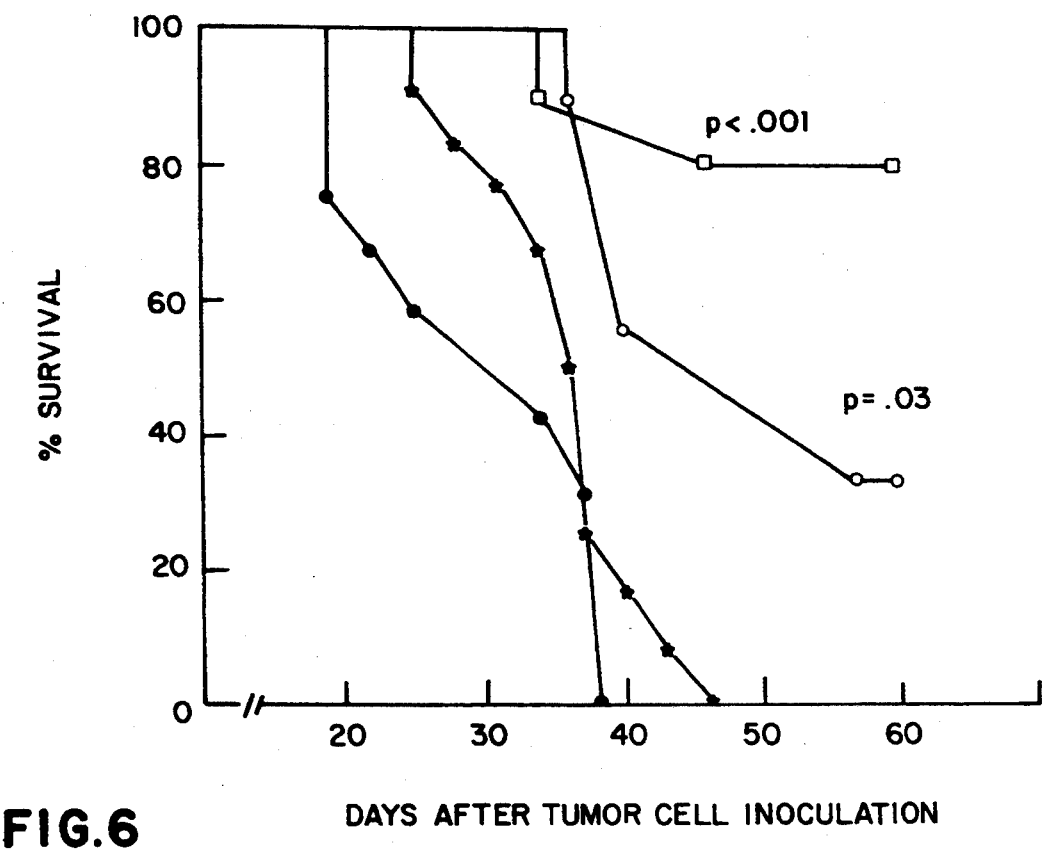
FIG. 6    DAYS AFTER TUMOR CELL INOCULATION

GROWTH REGULATION AND RELATED APPLICATIONS OF OPIOID ANTAGONISTS

This is a divisional application of copending application Ser. No. 740,972 filed Aug. 6, 1991 now U.S. Pat. No. 5,266,574, which is a continuation application of application Ser. No. 900,575, filed Aug. 26, 1986, now abandoned, which is a continuation-in-part of U.S. Ser. No. 598,092, filed Apr. 9, 1984, now U.S. Pat. No. 4,689,332.

BACKGROUND OF THE INVENTION

The present invention relates to a method for regulating the growth processes in a myriad of cells, tissues, organ systems and unicellular and multicellular organisms. More specifically, in accordance with the present invention, the fundamental growth processes in a multitude of biological systems can be modulated by the administration of the opioid antagonists naloxone, naltrexone, their analogs, metabolites, and/or derivatives.

In the past, naloxone and naltrexone have been employed predominantly for the treatment of narcotic addiction. Specifically, these compounds reverse the narcotic effects of exogenous opiates and opiate-like substances such as heroin and morphine, acting antagonistically thereto on a biochemical level.

Naloxone, the first of these compounds to be synthesized in 1960, was shortly thereafter discovered to have "pure" antagonist character, i.e., exhibiting virtually no agonist activity. Thus, naloxone became the preferred regime for the treatment of acute narcoticism.

However, since naloxone exhibited a relatively short duration in the body, it became clear that a longer acting agent having similarly "pure" antagonist character would be even more advantageous. Naltrexone was thus developed in 1965 in order to fulfill this requirement and was found to have greater potency and longer action than its N-allyl cogener, naloxone.

Since the discovery, during the early nineteen-seventies, of endogenous opioid substances, i.e., a group of pentapeptides produced by the cells of the brain and pituitary gland, and with the discovery of specific endogenous opioid receptor sites, there has been considerable interest in uncovering the possible roles of these endogenous compounds and their receptors in a variety of physiological and pharmacological processes. Many studies relating to these naturally occurring opioids and opioid-like substances such as leucine enkephalin, methionine enkephalin, dynorphin and beta-endorphin, collectively referred to as endorphins, have used antagonism by naloxone and/or naltrexone as a criterion for implicating the endogenous opioids in certain biological processes. Although it had been assumed that neither antagonist has pharmacological action other than that related to blockade of the opiate receptor, recent studies have indicated that these compounds may have some independent biological activity.

Furthermore, the discovery of the opioid receptor has also been the focus of extensive biochemical investigation into the mechanisms of tolerance and dependence. For example, it is reasonably well established that both exogenous and endogenous opioids and opioid-like substances modulate the pain threshold through stereospecific binding at the site of the opioid receptor. It has been determined that the administration of a concomitant amount of the compounds naloxone or naltrexone act competitively at the level of the receptor site to elicit an effect antagonistic to the narcotic, i.e., acting to blockade the receptor site and thus prohibiting the interaction between the opioid and the receptor site. The analgesic effect of the opioid is thereby prohibited or eliminated.

Recent studies have also determined that the exogenous opioids, specifically heroin, have some effect on tumor growth. In particular, heroin has been found to retard tumor growth and prolong survival time in mice with murine neuroblastoma, a well-characterized tumor that resembles human neuroblastoma. Moreover, it was found that this action could be blocked by the concomitant administration of the narcotic antagonist naloxone.

Although the opioids, their interrelationship with the respective narcotic antagonists and the stereochemical interaction which takes place-at the site of the opioid receptors have all been the focal point of intensive investigative research, a litany of inconclusive results and seemingly contradictory observations have left much of this biochemical and physiological phenomenon substantially enigmatic. For example, fairly recent research has shown that, at certain levels, the administration of naloxone blocks the tumor growth-inhibitory effects of heroin. However, naloxone used alone, also demonstrates growth inhibitory action on tumorogenesis.

Therefore, in-view of this unreconciled data, an accurate receptor model of opioid action has not been designed heretofore, and more significantly, the role of the endogenous opioid system as a fundamental factor in controlling the growth processes of most biological systems has gone unrecognized.

The present invention, however, provides a consistent model for opioid receptor action which has been surprisingly discovered to involve the control of certain fundamental aspects of endogenous growth modulation in a myriad of living organisms.

SUMMARY OF THE INVENTION

It is therefore one object of the present invention to provide a method for regulating the growth processes in a myriad of cells, tissues, organ systems and unicellular and multicellular organisms including plants and animals.

Another object of this invention is to provide a method for the prevention, treatment and control of cancer and related abnormalities.

Still another object of the present invention is to provide a method for accelerating the growth and development of animals and plants in order to increase food production and food availability.

Another object of the present invention is to provide a method for increasing the in vivo and/or in vitro production of cells, tissues, organ systems and unicellular plants and animals.

A further object of this invention is to provide a method for enhancing the wound healing processes in humans and animals.

A still further object of this invention is to provide a method for weight regulation in humans and animals.

Still another object of the present invention is to improve any method, system, technique or process which utilizes the biological activity of specific cells and/or organisms by regulating the growth processes of the cell or organism employed in such method, system, technique or process as desired.

These and other objects of the present invention are achieved by the administration of, or treatment with, the opioid antagonists naloxone, naltrexone, their analogs, derivatives, metabolites and/or mixtures thereof in an amount sufficient to effect the desired growth regulation in living organisms including a myriad of cells, tissues, organ systems and unicellular and mutlicellular organisms including plants and animals. At the cellular level these growth processes entail all mitotic related activity including cell proliferation, as well as cell migration and cell differentiation. At the somatic organismal level, these growth processes include anatomical, behavioral and neurobiological development, metamorphosis and maturation. Moreover, the method of growth modulation contemplated by the present invention includes both growth stimulation and growth inhibition and can be effected in vivo and/or in vitro.

BRIEF DESCRIPTION OF THE DRAWINGS

FIG. 1 is a graphic illustration depicting the effect on body weight of preweaning rats given daily injections of naltrexone of varying concentrations.

FIG. 2 is a graphic illustration depicting the effect of daily injections of naltrexone of varying concentrations on survival time of mice inoculated intradermally with S20Y neuroblastoma cells.

FIG. 5 is a graphic illustration depicting the variance in latency response in mice (challenged with morphine) tested on a hot-plate after subsequent treatment with varying concentrations of naltrexone.

FIG. 6 is a graphic illustration depicting the effect on survival time of mice inoculated subcutaneously with $10^6$ S20Y neuroblastoma cells receiving treatment with varying concentrations of naltrexone.

DETAILED DESCRIPTION OF THE INVENTION

Figure 3:
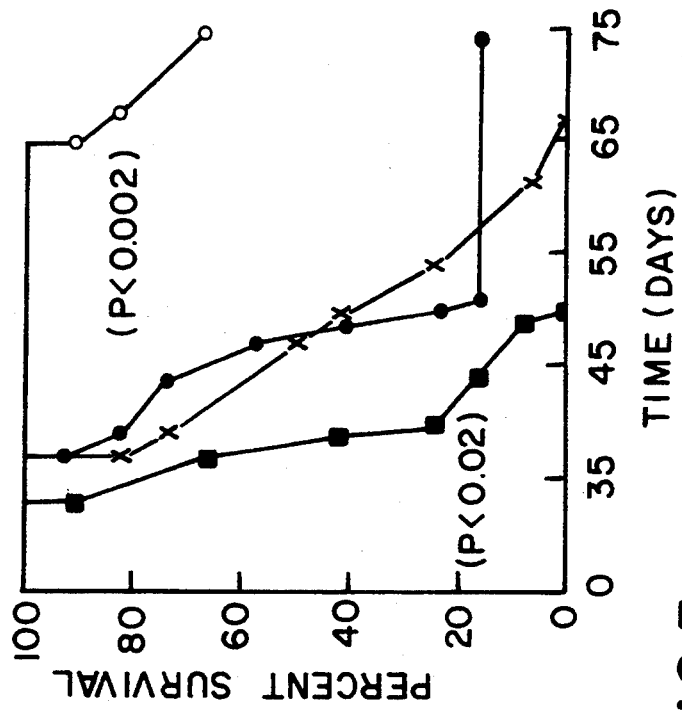
FIG. 3 is a graphic illustration depicting the effect of daily injections of naltrexone of varying concentrations on survival time of mice inoculated subcutaneously with S20Y neuroblastoma cells.

In accordance with the present invention it has been incredibly discovered that the fundamental growth processes in a multitude of "developing" organisms, i.e., capable of mitotic activity and related processes, including cells, tissues, organ systems and unicellular and multicellular organisms including vertebrates, invertebrates, plants, mammals and man can be regulated by the administration of, or treatment with, the opioid antagonists naloxone, naltrexone, their analogs, derivatives, metabolites and/or mixtures thereof. At the cellular level these growth processes entail all mitotic events and related processes including cell proliferation, as well as cell migration and cell differentiation. At the somatic or organismal level these growth processes include anatomical, behavioral and neurobiological development, metamorphosis and maturation. Moreover, these growth processes can be accelerated or decelerated as desired, and can be effected in vivo and/or in vitro.

More specifically, this growth modulation is effected through the stereospecific binding of the above compounds at the site of the opioid receptor. It has been discovered herein that cellular and somatic or organismal growth can be stimulated, as desired, by the administration of the present opioid antagonists in an amount which effectively "saturates" the opioid receptors, i.e., a threshold amount which effects complete blockade of the receptor sites from interaction with endogenous and exogenous ligands for a continuous period of time. In otherwords, it has been determined that as long as the cellular receptor sites are completely occupied by the antagonist, growth stimulation, i.e., growth acceleration, will be operative for the period of time in which the sites are effectively blocked. This period of blockade, therefore, is a function of the threshold dosage required to effectively saturate the receptor sites and the rate at which the opioid antagonist molecule is removed from the site, e.g., metabolically.

The mechanism responsible for growth inhibition, i.e., growth termination, being somewhat more subtle, is apparently responsible for the seemingly conflicting experimental data obtained, heretofore. Accordingly, it has presently been discovered that cellular and somatic or organismal growth inhibition, i.e., growth deceleration or growth termination, is facilitated by the administration of a dosage regime of the selected opioid antagonist which only temporarily saturates the opioid receptor. This format induces a cellular or somatic biofeedback response which promotes an endogenous growth inhibiting or growth terminating effect.

More specifically, it has been found that, although cellular and somatic growth can be accelerated in an "uncontrolled" state during the time period in which the receptor site is completely blocked, growth inhibition or growth deceleration, however, is effected by "intermittently" removing the blockade during a prescribed period of time and permitting the endogenous opioids or opioid-like substances to act at the receptor sites to terminate the growth response. Furthermore, this discovery has also led to the development of an extremely consistent receptor model by which the fundamental growth control mechanism can be better understood. The present model is also capable of explaining many of the discrepencies and inconsistencies observed heretofore.

It is believed that any given developing or proliferating cell, including tissue cells, organ system cells, all other somatic cells and the cells of unicellular and multicellular organisms including vertebrates, invertebrates, plants and man, is naturally provided with anywhere from one to about three-hundred thousand opioid receptor sites which are now believed to effect mitotic activity and related processes at the cellular level.

While not wishing to be bound, it is believed that during cellular growth and replication and during organismal development, i.e., during ontogeny, growth is modulated at the cellular level by the production of certain endogenous opioid products and/or opioid-like substances, e.g., endorphins, which are either produced by the particular cell itself or, in the more complex multicellular organisms, also by other more specified cells, e.g., the brain and pituitary gland in mammals and man. These substances, when stereospecifically bound at the receptor site, appear to inhibit the cellular growth response at a prescribed interval during the natural course of cell proliferation and somatic development. This process appears to be effected through a certain biochemical feedback system which may or may not entail other metabolic products and/or metabolites. Furthermore, it has now been discovered that when naloxone, naltrexone, their analogs, derivatives, metabolities and/or mixtures thereof are administered to the cell in a dosage which effectively saturates these receptor sites, i.e., when the antagonist compounds stereospecifically occupy the receptor sites, the "signal" for the onset of the cellular growth processes is initiated and/or allowed to continue. As long as the opioid site is blocked from the interaction with the opioid compounds endogenously produced, the cell will grow in an "uncontrolled" state, maximally compressing the temporal growth sequence with no avenue to terminate the growth signal until it reaches a biological limit, i.e., the upper limit of its biological capabilities defined by a genetic domain. Hence, at the cellular level, whether the cell is cultured in vitro or grown in vivo, the growth phase continues unimpeded, subject to media depletion and other environmental limitations. These growth processes at the cellular level entail all mitotic events and related processes leading to cell proliferation, cell migration and cell differentiation. At the somatic level, although multicellular organisms treated with naloxone and/or naltrexone do not generally grow in size, mass or weight beyond their genetically prescribed parameters, the treated subjects do exhibit accelerated growth and development to maturity three to five times faster than normal and can appear up to 33% larger than untreated subjects (controls). Thus, the temporal sequence of growth is substantially compressed by the action of the antagonist compounds of this invention but are not responsible for the creation or destruction of cellular mass.

The treatment or administration of the present compounds can also manipulate the normal sequence of cellular and somatic or organismal growth events to induce growth inhibition as well. By way of explanation, it is postulated that during the period when complete blockade of the receptor sites is sufficiently established, e.g. when an amount of naltrexone is administered which is sufficient to stereospecifically bind the receptor sites to the extent of effective saturation, three sequential biofeedback responses are induced. First, the number of available receptor sites is increased in each affected cell. Secondly, there is a concomitant increase in each affected cell's "sensitivity" or "susceptibility" to an appropriate opioid molecule, whether provided exogenously or endogenously. Finally, a heightened production of the endogenous opioid substances is elicited, for example, inducing high level production of endorphins and/or endorphin-like substances. While the sites remain effectively blockaded by the antagonist compound, the cell remains in a state of accelerated growth. Termination of this "uncontrolled" condition of stimulated growth can not be effected until the endorphin compounds are permitted to occupy the opioid receptor sites, thereby "turning off" the cellular growth signal. When the blockade is removed, e.g., metabolically, the induced growth phase is terminated by the operation of the over-production of the endogeneous substances.

The course of these sequential events can therefore be utilized to manipulate the production of endorphins or related endogenous compounds during the natural growth phase, i.e., during ontogeny, in such a manner as to actually inhibit the growth of the target cells or subject organism. Thus, for example, the growth of rapidly growing cells which characterize carcinogenic growth patterns can be terminated through increased endogenous opioid production employing naloxone, naltrexone, their analogs, derivatives, metabolities or mixtures thereof by acting on cells that contain an increased number of receptors and which are supersensitive to the opioid molecule.

Thus, according to the present invention, it has been determined that only two factors are critical in regulating the temporal growth sequence in most known cells. Primarily, it is first necessary that the subject cell is characterized by the presence of at least one opioid receptor. Obviously, in multicellular animals and plants the target cells must be characterized by the presence of these sites. This determination can be easily facilitated by conventional means as described below. The second requirement is that the threshold amount of the selected antagonist compound necessary to effect complete and continuous blockade of the receptor sites for the necessary duration is established so that the desired growth results can be obtained. In this regard, it is important to note that growth modulation is a function of the duration of effective blockade and is not dosage dependent, per se. (This is demonstrated in Examples 5 and 6 below.) Both critical aspects of this invention as herein described can be easily ascertained by one ordinarily skilled in the art in the absence of undue experimentation.

For example, binding assays of [$^3$H] methadone, [$^3$H] naloxone, [$^3$H] naltrexone and the like, carried out on cell homogenates can be employed to radioactively "tag" the opioid receptor sites in the subject cells. This technique permits easy determination of the presence of the opioid receptor. Once the presence of the receptor site has been determined, the cell is then known to be susceptible to the method of growth regulation of the present invention. Alternatively, standard autoradiographic techniques can be utilized to determine the presence and localization of the opioid receptors.

Of course, these in vitro techniques need only be employed where the cell or the organism identified is not previously known to possess opioid receptor sites.

However, at this time most cells, cell-types and organisms, particularly developing organisms and developing and proliferating cells have been determined to possess these receptor sites.

In any event, at the cellular level, dosage requirements can be conveniently ascertained. The subject cells are first cultured conventionally to determine a standard growth cycle, i.e., a growth curve. Subsequently, comparative growth cycles are established by providing the growth media with any one of the opioid or opioid-like substances which are known to bind at the opioid receptor and thereby effect growth inhibition. Examples of these known compounds are morphine and heroin. At the point where cell growth is abruptly interrupted relative to the previously established standard cell growth curve, complete occupation of the opioid receptor site has been effected. Once this concentration is determined, the desired growth regulation can be effected by manipulating the dosage regime of opioid antagonist treatment in accordance with this invention. In other words, at this concentration it is known that the concomitant administration of the present antagonist compounds will completely saturate the receptor sites and thus meet the threshold requirement where accelerated growth is induced. This agonist-antagonist correlation is consistent and represents, absolutely, the point at which opioid site saturation is effectively completed. For example, cells subject to a range of about $10^{-3}$ to about $10^{-8}$M concentration of naloxone, naltrexone, their analogs, derivatives, metabolites and/or mixtures thereof will initiate "uncontrolled" cell proliferation which is limited only by media depletion and other environmental limitations. The subject cells treated with this range of concentrations continue to proliferate and undergo mitotic events at a rate three to five times greater than normal. Concentrations of $10^{-6}$M are preferred.

For purposes of establishing the saturation threshold in higher animals including invertebrates, vertebrates and mammals, several tests have been employed. Pain threshold tests, for example, are based on the determination that at the point of complete blockade, the analgesic effects of the opioids such as morphine, heroin, methadone and the like, are eliminated. Examples of conventional pain determination tests used in animal studies which can be employed to determine receptor site saturation levels are, for example, the hot plate test, acetic acid-induced writhing, threshold titrated foot-shock, the tail-flick test, escape from tail pinch tests and formalin-induced pain tests and the like. Tissue concentrations can also be readily ascertained by conventional assay methods such as, for example, by high pressure liquid chromotography (HPLC). Once the saturation level is determined, growth modulation can be manipulated in accordance with the regime described above in order to effect the desired results.

Dosage regiments for human subjects are fairly well established since naloxone and naltrexone have long been employed for the treatment of drug addiction. Inasmuch as the dose which is required to overcome objective and subjective heroin or morphine related responses operate by effective blockade of the receptor sites, these dosage schedules are easily applied to effect the desired growth modulation in accordance with the present invention, particularly since the agonist-antagonist correlation is absolute. Moreover, objective and subjective heroin or morphine related responses which are blocked by naloxone and naltrexone generally correlate strongly with plasma levels of the compound and therefore can be easily ascertained to suit individual requirements.

The dosage requirement necessary to effect complete blockade of the receptor site in man for a period of twenty-four hours range-s from about 20 mg and above and can be administered orally, in liquid or pill form, parenterally, intraveneously or by any other conventional delivery mode such as, for example, microcapsules, spherical bead implants, suspensions, osmotic minipumps, and the like.

Maintenance determination of opioid blockade can also be readily ascertained by two clinical techniques which quantitatively measure the metabolism of these compounds in biological fluids. In particular, thin layer chromatographic (TLC) separations and gas liquid chromatography (GLC) procedures using flame ionization and electron capture detectors have been successfully employed.

Thin layer chromatographic separation of naloxone, naltrexone, 6-beta-naltrexol, and other analogs or metabolites can be achieved on silica gel plates. For example, an aliquot of the first morning urine is adjusted to pH 8.5 with a carbonate buffer and extracted into chloroform. The organic phase is separated and taken to dryness. The residue is redissolved and the enriched sample is spotted onto a silica plate. The chromatogram is developed in methanol/water/ethyl acetate (1:1:29) in the presence of ammonium hydroxide (10 ul) and the coloration is enhanced by exposing the plate to 37% formaldehyde fumes. Visualization is achieved by dipping the chromatogram into Mandelin's and Dragendorff's reagent. Effective opioid receptor blockade is achieved at plasma levels in excess of about 2.0 mg/ml.

Plasma samples can also be analyzed for these compounds by adjusting the pH of plasma aliquots to 8.5 with bicarbonate buffer and extracting the antagonist into chloroform. The compound is then back extracted into a weak acid from the organic layer. The acid phase is neutralized and adjusted to pH 8.5 with bicarbonate buffer and reextracted into chloroform. The organic phase is evaporated and the residue reconstructed with pentafluoropropionic anhydride, the anhydride is evaporated and the residue redisolved in ethyl acetate and injected onto a 3% OV-22 (80–100 mesh) column. Chromatographic separation is achieved isothermally at 215° C., carrier gas is 10% methane in argon (35 mi/min) and detection is achieved with an absolute sensitivity of 5–10 pg by a Ni electron capture detector.

Figure 11:
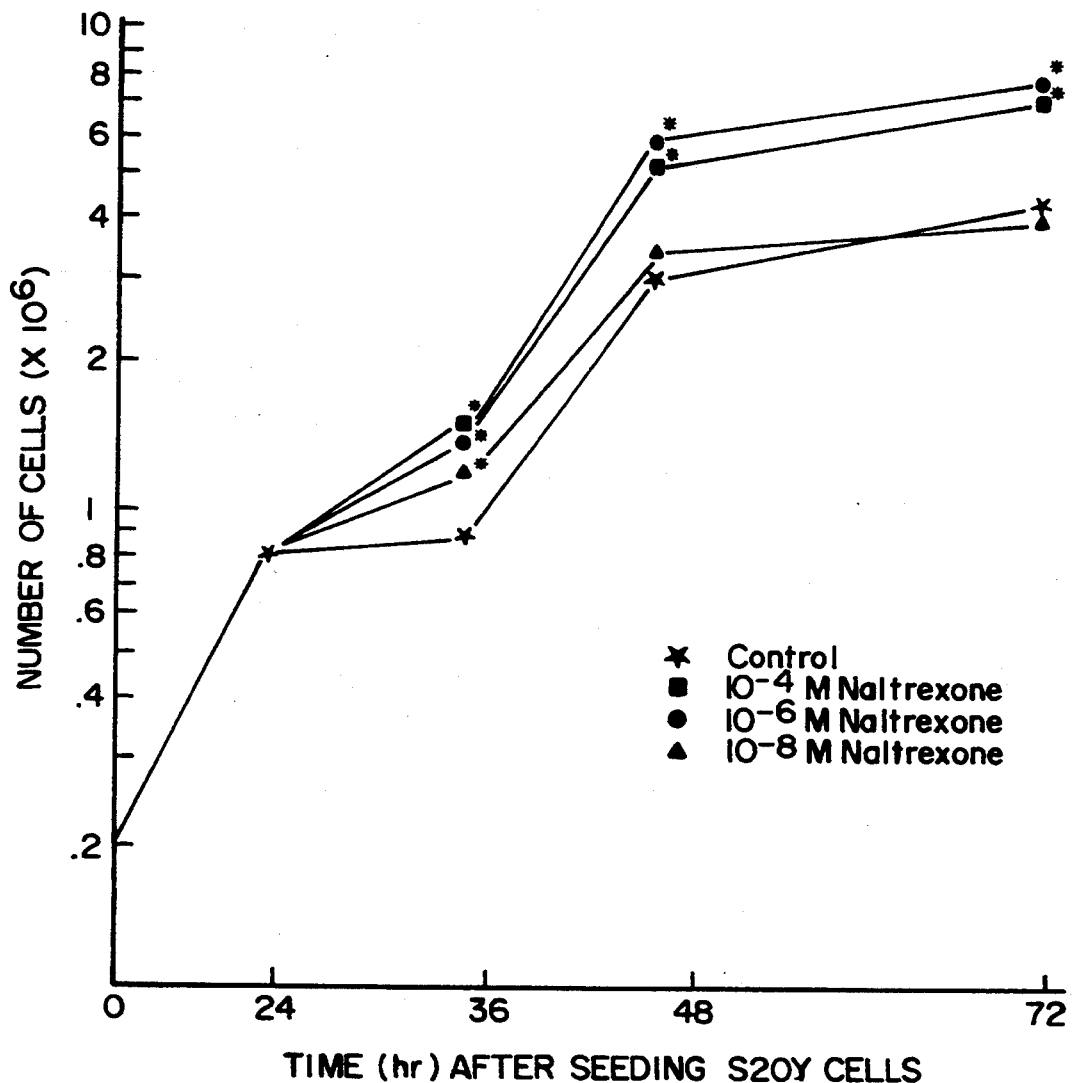
FIG. 11 is a graphic illustration depicting the effect of naltrexone upon the growth rate (per unit time) of S20Y neuroblastoma cells in culture.

Thus, in one embodiment of the present invention, the acceleration of cellular growth is effected in vitro by the administration of naloxone, naltrexone, their analogs, derivatives, metabolites and mixtures thereof to culture media containing the subject cells in amounts ranging from about $10^{-3}$ to about $10^{-8}$M concentrations. Specifically included in this aspect of the present invention is the accelerated growth of cells in culture (see, Example 7 and FIG. 11) and the accelerated growth of bacteria (see, Example 8). The continued acceleration of all mitotic events and related cellular processes is preferably effected at $10^{-4}$ to $10^{-6}$M concentration. This simple procedure effecting growth acceleration can be successfully employed with any developing or proliferating cell, i.e., which retains the ability to undergo mitotic activity, including tissue cells, organic system cells or unicellular animals or plants which are characterized by the presence of at least one opioid receptor site. Such determination can be readily made as described hereinabove. This application is particularly useful for rapid preparation of hybridoma cultures which are employed for the production of a wide range of useful products.

The analogs, derivatives and metabolites of naloxone and naltrexone include, for example, beta-FNA (beta-fumaltrexamine), 6-beta-naltraxol, naloxazone, BIT ([2-p-ethoxy-benzy]-1-diethylaminoethyl-5-isothiocyanobenzimidazole-isothiocyanate), FIT (fentarylisothiocyanate), FAO (fumaramide oriphavione) and experimental derivatives, such as M154,129. Futhermore, the terms narcotic antagonists, opiate antagonists and opioid antagonists as used herein, mean all natural and synthetic products which have the pharmacological efficacy to antagonize opioid or narcotic induced analgesia.

In another specific embodiment of this invention, growth stimulation in animals, including vertebrates and invertebrates, can be effected by the cumulative administration of at least about 10 mg/kg of the present compounds and preferably amounts of 20 mg/kg or above. Although the dosage schedule can vary according to the particular species, the key element is that the receptor site is occupied for the prescribed continuous period, e.g., 24 hours. Continuous blockade for a period of at least about 12 hours per day will successfully effect accelerated and increased growth in the animal subjects. A determination of the duration of effective blockade can be readily ascertained by the techniques described above. Accordingly, growth acceleration can be effected about three to five times greater than normal in developing animals and size can be increased as much as about 33% relative to untreated animals, i.e., controls.

In order to effect growth inhibition in animals, including vertebrates and invertebrates, administration of the present compounds in a cumulative amount less than about 10 mg/kg per day is employed. Again, although the dosage regime can vary from species to species, the critical aspect is that complete blockade is effected for a duration of no less than about 2 hours, and up to a maximum of about 12 hours in a 24 hour period. Removal of the opioid antagonist from the receptor site after this duration will sucessfully effect cellular and somatic growth inhibition by operation of the endogenous mechanisms described above. Effective blockade for periods of 4 to 6 hours are preferred in order to effect growth inhibition in developing animals.

In a further embodiment of the present invention, cellular and somatic growth acceleration can be effected in humans, for example, in the treatment of developmental disorders, or in order to increase the proliferation, migration and differentiation of certain specific cells or tissue, including organ tissues, neural tissue, bone marrow, red blood cells, lymphocytes, liver cells, etc. Specifically, the administration of the opioid antagonists in cummulative amounts ranging from about 20 mg and above will successfully effect growth acceleration in the target cells of the human subject. Although these ranges will vary among individuals, a dosage schedule which effects complete blockade for a period of at least about 12 hours in a 24 hour period will induce the desired accelerated growth. This technique can also be particularly employed to effect weight gain in individuals requiring increased weight.

Depending upon the particular individual, a dosage schedule effecting growth inhibition, for example, in cases where it is desirable to effect weight loss, is facilated by the administration of these opioid antagonists in cumulative amounts of less than about 10 mg per day. Dosages totaling about 0.1 to about 1.0 mg can be effective for inhibiting cellular and somatic growth in humans. The critical duration of temporary blockade required to effect growth inhibition ranges from about 2 to a maximum of about 12 hours in a 24 hour period. Best results are achieved by effecting complete blockade for a period between about 4 to about 6 hours in a 24 hour period.

A further application of the present invention is related to the treatment and alleviation of pain and "addictive" behavior in man. Addiction or addictive behavior as used herein means an overwhelming physical or psychological need to continue use of a drug, chemical and/or substance such as, but not limited to, alcohol, tobacco, opioids or food. The endogenous opioid system, i.e., the receptor and the opiods produced by the body itself, have been implicated in the "dependent" use of nicotine, alcohol and various addictive drugs. It is postulated herein that such "addictive" behavior is physiologically manifest at the biochemical level by a "need" to have the opioid receptor site constantly occupied by a particular exogeneous opioid.

Pain, as used herein, meaning an unpleasant sensory or emotional experience, having a pathophysiologic and/or psychologic origin, associated with actual or potential tissue damage, or described in terms of such damage (*The Challenge of Pain*, New York, Basic Books, 1982, p. 71), can be alleviated as well. Notably, it has been observed that patients undergoing accupuncture therapy feel relief from pain and the symptoms of drug or alcohol withdrawal. Accupuncture is believed to elevate the endogeneous opioid level, thereby saturating the receptor site to a "satisfied" condition.

Accordingly, a regime for the treatment and alleviation of such symptomatic behavior and its underlying physiological manifestation, i.e., pain and addiction, can be implemented employing the opioid antagonists of this invention. Not unlike several of the other embodiments herein, pain and addictive behavior can be controlled by the administration of an intermittent regime to the subject, i.e., low dosages, of naloxone, naltrexone, their analogs, derivatives, metabolites and mixtures thereof.

Specifically, pain and addictive behavior in man can be treated, i.e., alleviated, by the administration of the present antagonists in amounts which temporarily blockade the opioid receptor thus eliciting the "heightened" response herein described, i.e., increased production of the endogeneous opioids and the cells increased sensitivity thereto. Regimes which temporarily blockade the sites for a duration of at least about 2 hours and no more than about 12 hours in a 24 hour period will elicit the appropriate response. Regimes of less than about 10 mg per 24 hour period will effect the requisite temporary blockade in man although dosage variations are easily ascertained in accordance with the techniques herein described. For example, dosages totaling about 0.1 to about 1.0 mg per day can be effective to alleviate the symptoms of addictive behavior in some subjects.

In several further embodiments of the present invention, the growth modulation procedures described herein can be implemented in any process which utilizes the activity of biological systems, e.g., the metabolic activity of bacteria and, more specifically, in any process wherein it would be advantageous to accelerate the production of the cells, bacteria or other organisms which are employed. For example, the present method can be implemented in any fermentation process, such as, for example, in processes for the production of alcohol, vinegar, milk products and the like. The economics and operational efficiency of sewage effluent plants can be enhanced by employing the present growth procedures to increase bacterial availability for metabolizing sewage waste. Food sources covering the entire food chain can be increased by treatment with, or administration of, the present compounds. Thus, food availability can be increased for human consumption both directly and indirectly, e.g., by the increased growth of plankton upon which fish feed. Cell and tissue regeneration techniques can be enhanced by employing the growth procedures of the present invention by accelerating the growth of the related cells and tissues including, for example, regeneration of spleen and liver tissue, increasing production of red blood cells, lymphocytes, regeneration of the epidermis, bone-marrow and connective tissue, such as muscle and cartilage. Moreover, many other medical techniques can be improved by accelerating the growth of tissue cells including, for example, transplantation of fetal and neonatal tissue, the regeneration of tissue and particularly transplant tissue such as required by skin grafting techniques related to the treatment of burn victims, and transplant techniques for neural and connective tissue related to the treatment of brain and spinal cord injuries. In fact, any process, whether requiring an in vitro or an in vivo procedure which incurs an advantage by accelerating cellular or somatic growth can be enhanced by employing the growth modulation method of this invention. Generally, any process which utilizes the metabolic or related biological activity of living organisms, for example, bacterial cells, may be made more efficient by incorporating the present procedures to accelerate cellular growth and increase cellular availability. Accordingly, even methods for the bacterial reduction of sulfur in coal and methods for the clean-up of oil spills, can be enhanced, i.e., by increasing bacterial proliferation and production.

It is another aspect of this invention that, upon diagnosis of uterine growth retardation syndrome or any related fetal growth disorder, for example, a regime of naloxone, naltrexone or any of their effective analogs, derivatives or metabolites, can be developed in order to accelerate fetal growth to its normal state. Such a growth regime can accompany diagnosis by sonography, amniocentesis and other diagnostic techniques.

Wound healing procedures, especially, can be enhanced dramatically by accelerating the growth and mitotic events of the wounded tissue and related cells, e.g., fibroblasts, in order to increase collagen production and promote healing granulation. Fiber production can be facilitated in culture or in vivo at increased rates according to this invention and subsequently or concurrently applied to wounded areas by layering or other techniques including implanting subcutaneous pumps, beads, etc. Skin grafting, for example, utilized in the treatment of burn victims can be greatly enhanced by the accelerated growth of the tissue to be grafted.

In another embodiment of this invention, weight control can be facilitated. As described above, complete blockade of the receptor sites will induce "uncontrolled" growth at the cellular level and in time will cause an increase in overall body weight due to an increase in fat cell size and an increase in fat cell numbers.

On the other hand, a regime of the present compounds can be devised which, as described above, would effect temporary blockade of the receptors and thus inhibit cell growth, i.e., expansion and/or increase of fat cells will be inhibited and apparently, to some extent, reduced. Weight of the subject can therefore be held at a constant level or at least within a prescribed range.

One of the most significant embodiments of the present invention is related to the prevention, treatment and control of cancer. The action of the compounds of the present invention can be employed to terminate the rapid cell growth which characterizes the abnormal growth patterns of cancer and related abnormalities. It should be understood, however, that a regime of the present compounds cannot dissipate or reduce a tumor mass or any other metastasized growth. These compounds can only terminate the growth of the abnormal cells and inhibit the continued growth thereof. However, by preventing tumor growth to continue i.e., reducing the tumor burden, the body's own defense mechanisms, i.e., the immune system, has the opportunity to rid the body of the cancerous growth whether benign or malignant. This aspect of the invention is particularly significant in light of early diagnostic techniques which can be coupled with conventional chemotherapy which does reduce tumor size, or with procedures for tumor excision. Moreover, naloxone, naltrexone, or the other related compounds can be administered as a prophylaxis to human or animal subjects who may be exposed to potentially carcinogenic agents. By administering an intermittant regime of the antagonists before, or soon after, exposure to such agents, thereby temporily effecting blockade as described above, the body heightens production of the endogenous opioid levels and tumor take is avoided, the immunological system of the body being permitted to work effectively since rampant abnormal cell growth is minimized or eliminated. For example, administration of the present antagonists in cumulative amounts less than about 10 mg per 24 hour period will effectively inhibit tumor take in humans while cumulative amounts less than about 10 mg/kg per day will be effective for animal subjects. In terms of duration, the proper endogenous response is elicited by effecting a temporary blockade of either subject's opioid receptors for a duration of at least about 2 hours and no more than about 12 hours in a 24 hour period.

More specifically, for example, subsequent to the diagnosis of an aberrant growth, a biopsy is taken to determine the nature of the growth and to verify the presence of opoid receptor sites. Once this determination is complete, i.e., that the abnormal growth is characterized by the presence of at least one opioid receptor site, a dosage schedule which will terminate the growth of the cell is determined as described above. Dosages of less than a total of 10 mg per day for human subjects or a cumulative amount less than about 10 mg/kg per day for animal subjects, or a temporary duration of effective receptor blockade for at least about 2 hours and no more than about 12 hours per day in either case will successfully inhibit growth and reduce the tumor burden.

It should be readily understood that the method of the present invention for regulating cellular and somatic or organismal growth can be applied wherever the acceleration or deceleration of cellular growth and related mitotic activity, e.g., production of metobolic products, is advantageous. Thus, in view of the nature of this invention, the above examples must be understood as absolutely non-limiting.

For a better understanding of the present invention together with other and further objects, reference is made to the following descriptions and examples.

EXAMPLE 1

Animals. Newborn animals (day 0) from random-bred Sprague-Dawley female rats were culled to 8 pups per mother. Beginning on day 1, pups were given daily SC injections of either 1 or 50 mg/kg naltrexone or sterile water (control) until weaning (day 21). Solutions of naltrexone were prepared by dissolving naltrexone (Endo Laboratories, Garden City, N.Y.) in sterile water. Rat pups were weighed on days 3, 5, 7, 10, 15, and 21 and appropriate dosage adjustments made.

Somatic Development. In addition to monitoring body weights during preventing development, the wet weights of selected organs were determined on day 21. At weaning, animals were overdosed with chloral hydrate and autopsied. The following organs were removed, blotted free of blood, and weighed: brain, heart, kidneys (both left and right), liver, skeletal muscle (right M. triceps surae). At least 12–18 animals/group, with an equal representation of males and females, were examined.

Behavioral Ontogeny and Physical Characteristics. Beginning at 5 days of age, the development of spontaneous motor behavior (i.e., walking) and physical characteristics were assessed. Animals were individually placed in the center of a 55×55 cm examination table covered with Durasorb laboratory underpad and observed for the appearance of walking. Walking was defined as traversing one body length with the abdomen not touching the surface. In addition to recording the ability of an animal to walk, the time of appearance for 4 physical characteristics was recorded. Eye opening was defined as a visible break in the eyelid and membrane covering; ear opening as an opening of the external auditory meatus; incisor eruption as the appearance of upper incisors; and hair covering as the appearance of a complete coat of white hair.

The age at which walking or a physical characteristic first appeared for any group member (equaling the age of initial appearance) and, the age at which 100% of the animals demonstrated a particular behavior (equals the age of maximal response) were recorded.

Statistical Analyses. Body weight and organ weights were analyzed using a two-factor analysis of variance with Group and Sex and independent variables. Subsequent planned comparisons were performed using Newman-Keuls tests. Data on behavioral tests were analyzed. In brief, overall differences in the age of appearance of walking or physical characteristics were analyzed using the Median Test. If this test revealed significance, subsequent comparisons were made between each experimental group and the controls using the Fisher Exact Probability Test.

RESULTS

Data on body weights (FIG. 1) showed that naltrexone altered weight gain depending on the dose administered. Rats injected with 50 mg/kg had increases in body weight over controls by 3 days of age. Significant increases in body weight were recorded in the 50 mg/kg naltrexone group throughout the preweaning period and by day 21, this group of rats weighed 18% more than controls. Rats injected with 1 mg/kg naltrexone were subnormal in weight during the preweaning period and weighed 11% less than controls at 21 days.

Consonant with the data on body weight, the effect of naltrexone on organ growth was dose-related. The wet weights of organs (Table 1) from 21-day old rats given 50 mg/kg naltrexone were elevated 11–32% in relationship to control organ weights. In contrast, the wet weight of organs from the 1 mg/kg naltrexone group were 5–24% below normal. Skeletal muscle was the organ most affected by naltrexone administration.

Calculation of relative organ weights (i.e., organ to body weight ratios), indicated that the changes in organ wet weight of naltrexone-treated animals were generally proportional to that of body weights with only two exceptions. In the 50 mg/kg naltrexone group, brain weight was significantly ($p<0.01$) less affected (18%) than body weight, whereas the weight of skeletal muscle was significantly ($p<0.05$) more affected (20%) than body weight.

In regard to the timing of appearance of certain physical characteristics, the 50 mg/kg naltrexone group exhibited a significantly earlier appearance of eye opening than controls, whereas the 1 mg/kg naltrexone group showed a significant retardation in the proportion of animals with ear and eye opening on the median day (Table II). The initial appearance of walking, a milestone in behavioral ontogeny, appeared 2 days earlier in the 50 mg/kg naltrexone group, relative to controls. Furthermore, at the age when only half (50%) of the controls were able to walk, no rat in the 1 mg/kg naltrexone group could walk (Table II).

EXAMPLE 2

Adult male syngeneic A/Jax mice (Jackson Laboratories) were inoculated intradermally in the right shoulder with $10^6$ S20Y neuroblastoma (NB) cells, cloned from the A/Jax mouse C1300 NB (Dr. M. Nirenberg, NIH, Bethesda, Md.). The day of tumor cell inoculation was considered day 0. Individual tumors were measured in 2 dimensions with vernier calipers (accuracy ±0.05 mm) every 3 days. Since tumors grew in somewhat irregular shapes, the largest dimensions perpendicular to each other were measured (a,b) and the diameter of each tumor was calculated by the formula: $(a \times b)^{\frac{1}{2}}$. The time of 'initial' appearance of a tumor was considered to be the date at which time tumor diameter was 5mm or larger. At the time of death, all mice were autopsied and a careful record of metastases and lesions made.

Beginning 2 days after tumor cell inoculation, animals received a daily s.c. injection of 0.1 mg/kg or 10 mg/kg NTX (naltrexone) (Endo Laboratories, Garden City, N.Y.) or sterile water (0.2 ml) in the intrascapular region. Animals were weighed weekly and appropriate dosage adjustments made. Injections of NTX and sterile water were continued throughout the experimental period until the death of all tumor-bearing animals.

Total survival time for all groups of mice inoculated with NB (including those animals that did not develop a measurable tumor) were analyzed using a two-tailed Mann-Whitney U-test. Survival time prior to tumor appearance, latency after tumor appearance, as well as total survival time of tumor-bearing mice were analyzed using analysis of variance; subsequent comparisons were made with the Newman-Keuls test.

The growth of tumors was compared for each mouse beginning on the day a measurable tumor was observed and every 3 days thereafter until day 24 (a time when at least 50% of all mice were dead). Tumor measurements on these days, as well as on the day of death, were analyzed with analysis of variance and Newman-Keuls tests. Body weights were compared with a two-factor analysis of variance.

RESULTS

Within 18 days after tumor cell inoculation, 100% of the mice in the control and 10 mg/kg NTX groups had measurable tumors, whereas only 44% (7 of 16 mice) in the 0.1 mg/kg NTX group had tumors at this time. On day 54 after tumor cell inoculation, when every other tumor-bearing mouse in all groups had died, 5 of 16

(31%) mice in the 0.1 mg/kg NTX group had not developed tumors; this proportion was significantly (P 0.01, chi-square test) different from both control and 10 mg/kg NTX animals (FIG. 2). Although the experiment was terminated when all tumor-bearing mice were dead (i.e. day 54), the remaining 0.1 mg/kg NTX mice were observed for 25 additional days and no tumors developed.

Total survival time, as well as length of survival before and after the appearance of a tumor, for mice in the 10 mg/kg NTX group were comparable to controls (Table 3). For mice in the 0.1 mg/kg NTX group, the median length of survival was 60% longer than control mice, whereas mean survival time was 43% longer ($<0.01$). The range of life expectancy was 39–54 days in the 0.1 mg/kg NTX group in comparison to a range of survival of 24–41 days for the control mice (FIG. 2). Evaluation of latency time from tumor inoculation to the appearance of a measurable tumor (Table 3) revealed that mice in the 0.1 mg/kg NTX group had a delay of 70% in contrast to control animals. Survival time after tumor appearance for those mice developing tumors in the 0.1 mg/kg NTX group was $26.1 \pm 1.8$ days; this value was significantly greater ($P<0.05$) than control levels ($20.84 \pm 1.4$ days).

With few exceptions, the pattern of tumor growth at the primary site was similar among all groups. Mean tumor size was significantly ($P<0.05$) increased for the 0.1 mg/kg NTX mice on day 6 after tumor appearance, and for the 10 mg/kg NTX group on days 6 and 9 after tumor appearance. However, at the time of death (Table 3), tumor size of NTX-treated and control animals was comparable.

Metastases (Table 4) were noted in all but 3 mice exhibiting primary tumors; 2 of these animals were of control group and 1 mouse in the 10 mg/kg NTX group. The most prevalent sites of metastatic growth were the lymph regions of the upper extremities (bilateral), followed by lesions of the lungs and liver. Infrequently, metastatic growths in the inguinal lymph nodes were recorded. The number of metastases per animal, as well as the proportion of metastatic lesions in each group were comparable between experimental groups. Although spleens from autopsied mice were weighed whenever possible, no significant differences in weights were recorded. Those mice not having tumors were killed and autopsied. Neither tumor growth at the primary site of inoculation, nor lesions in any organs, were observed. NTX had no effect on body weights of these adult animals.

EXAMPLE 3

Male syngeneic A/Jax mice were inoculated with S20Y neuroblastoma cells and, beginning 2 days later, received daily subcutaneous injections of either 0.1, 1, or 10 mg of naltrexone per kilogram of body weight or sterile water (control). On day 29 after inoculation with tumor cells, all mice in the 10 mg/kg and control groups had measurable tumors, whereas only 75 percent of the 1 mg/kg group and no animal in the 0.1 mg/kg group had developed measurable tumors. By day 75, when every other tumor-bearing mouse had died (FIG. 3), 10 of 12 mice (83 percent) and 4 of 12 mice (33 percent) receiving 1 and 0.1 mg of naltrexone per kilogram, respectively, had developed tumors. The percentage of mice developing tumors in the latter group differed significantly from that of the controls ($P<0.01$, chi-square test). Observations on the remaining mice for the next 25 days (that is, until 100 days after tumor cell inoculation) revealed no tumor development.

RESULTS

The survival time (FIG. 3) of mice receiving naltrexone (mg/kg) was comparable to that of control animals (mean and median life-spans = 50 days). Mice receiving naltrexone (10 mg/kg) survived for a significantly ($P<0.02$) shorter time than control mice (means and median life-spans 19 and 22 percent shorter, respectively, than control). Moreover, the latency prior to tumor appearance for this group was reduced 28 percent from control values ($21.25 \pm 1.23$ days). For those mice injected with naltrexone (0.1 mg/kg) that developed tumors, an increase in mean and median survival times of 42 and 36 percent, respectively, were recorded relative to controls, as well as a 98 percent increase in latency time prior to tumor onset.

Figure 4:
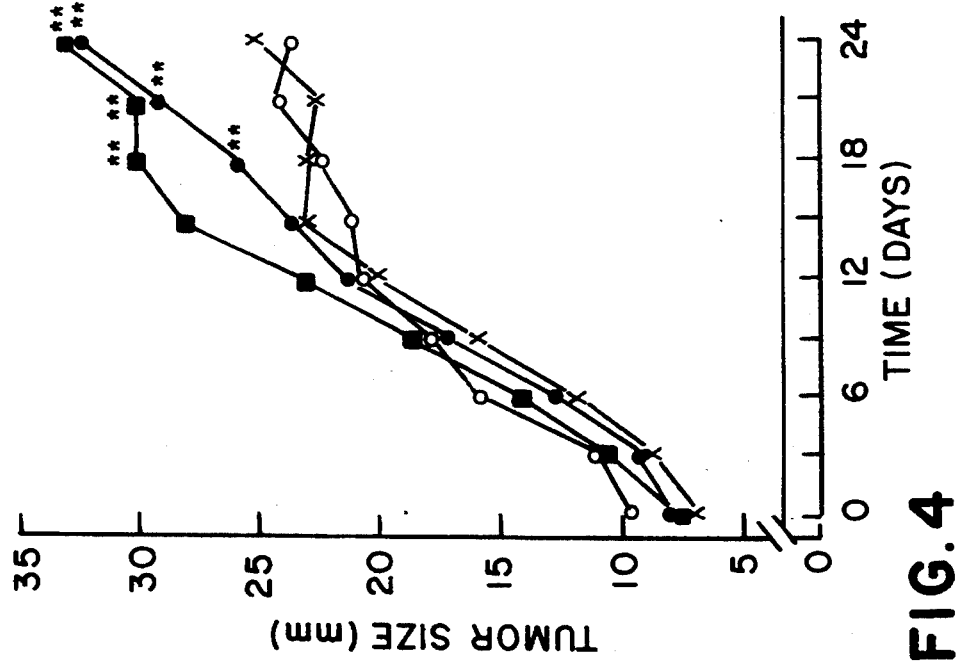
FIG. 4 is a graphic illustration depicting the effect on tumor size of mice receiving treatment with varying concentrations of naltrexone.

In general, the patterns of tumor growth for mice in the control and 0.1 mg/kg naltrexone groups were similar through the 24-day observation period (FIG. 4). The mean tumor sizes of mice injected with naltrexone (1 and 10 mg/kg) were similar to the case for controls for the first 15 days after the initial tumor appearance. However, on days 18, 21, and 24, tumors were significantly larger in both these groups. The average tumor size on the day of death was similar in all groups, except for mice in the 10 mg/kg groups, where tumor size ($32.4 \pm 1.8$ mm) was significantly larger ($P<0.01$) than that for controls ($26.2 \pm 0.8$ mm).

These results demonstrate that naltrexone can markedly alter the course of neural neoplasia, with the direction and magnitude of effects dependent on dosage. Naltrexone's major effect is to modify the interval between tumor inoculation and tumor appearance. The naltrexone dosages (0.1 to 10 mg/kg) mediating these effects were 0.02 to 2.0 percent of the LD50 [dose lethal to 50 percent of the animals tested, 570 mg/kg (5)] and did not elicit overt toxicological symptoms such as ataxia, convulsions, or loss of body weight. As evidenced in opiate challenge experiments (FIG. 5), the dosages of naltrexone used did invoke an opiate receptor blockade that lasted 4 to 6 hours per day at a dosage of 0.1 mg/kg, 12 to 24 hours per day at a dosage of 1 mg/kg, and the entire 24-hour period at a dosage of 10 mg/kg.

EXAMPLE 4

Newborn Sprague-Dawley rats, reared in litters of eight pups per mother, were given daily subcutaneous injections of naltrexone (50 mg/kg) or sterile water until 21 days of age (weaning).

RESULTS

Naltrexone-treated offspring had body, brain, and cerebellar weights that were 18, 11, and 5 percent greater than the control weights (Table 5). Macroscopic dimensions of the brain and cerebellum in the naltrexone-treated animals were 2 to 11 percent larger than those of the control animals (Table 5). Morphometric analysis of histological sections from the somatosensory cortex and cerebellum showed an enlargement of both regions in naltrexone-treated offspring (Table 6). In particular, areas of cerebellum analyzed were 41 to 45 percent larger than in controls. Further analysis of the cerebellum revealed increases in cellular content in sections of the pyramidal lobe (Table 7). The number of internal granule neurons per section was increased 30 percent and the number of glial cells (oligodendrocytes and astrocytes) in the medullary layer was increased 70 percent. The total population of glial, basket, and stellate cells in the molecular layer was increased 169 percent. Furthermore, the effect of naltrexone on cell number in the cerebellum appeared to be directed solely toward cell populations derived during the treatment interval, since Purkinje cells, which are generated prenatally, did not change in number with postnatal naltrexone exposure (Table 7).

These results demonstrate that naltrexone can markedly stimulate the course of somatic and neurobiological development in the rat. The dose of naltrexone mediating these effects (50 mg/kg) represented 2 to 3 percent of the median lethal dose for adult rats. This low dose antagonized morphine-induced analgesia completely and effectively. Measurement of Nociceptive responses (Analgesia Meter, Technilabs) 30 minutes after challenge with morphine sulfate (0.2 mg/kg) showed that the naltrexone blocked opiate receptors 24 hours a day.

EXAMPLE 5

Adult male syngeneic A/Jax mice (Jackson Laboratories) were inoculated subcutaneously in the right shoulder with $10^6$ S20Y neuroblastoma (NB) cells, cloned from the A/Jax mouse C1300 NB (Dr. M. Nirenberg, NIH, Bethesda, Md.). The day of tumor cell inoculation was considered day 0. Beginning 2 days after tumor cell inoculation, animals were divided into 4 groups and some received a single daily subcutaneous injection of either 0.1 mg/kg (=0.1NTX) or 0.4 mg/kg (=0.4 NTX) naltrexone (Endo Laboratories), or 0.2 ml sterile water (=controls). A fourth group of mice were injected 4 times daily with 0.1 mg/kg NTX (=4×0.1 NTX); injections were made approximately every 6 hr. All injections were made in the intrascapular region. Animals were weighed weekly and appropriate dosage adjustments made. Injections of NTX and sterile water were continued throughout the experimental period until the death of all tumor-bearing animals. At the time of death, all mice were autopsied and a careful record of metastases and lesions made.

Individual tumors were measured in 2 dimensions with vernier calipers (accuracy±0.05 mm) every 3 days. Since tumors grew in somewhat irregular shapes, the largest dimensions perpendicular to each other were measured (a,b) and the diameter of each tumor was considered to be that calculated by the formula: $(a \times b)^{\frac{1}{2}}$. The time of "initial tumor appearance" was considered to be the day at which tumor diameter was 5 mm or larger. The growth of tumors was compared for each mouse beginning on the day a measurable tumor was first observed and every 3 days thereafter until day 30 (a time when at least 50% of all mice were alive).

Opiate challenge experiments measured the latency of response (e.g., licking of paws) in mice tested on a hot-plate (55° C., Analgesia Meter, Technilabs). Morphine (0.2 mg/kg) was injected 30 min before testing. Animals were tested only once and they were removed from the hot-plate after 45 sec if no response was observed. Six mice each in the 0.1 NTX, 0.4 NTX and control groups were examined at 2, 4, 6, 10 and 24 hr. Mice receiving 0.1 mg/kg NTX four times daily were tested at the same time point; because of the repeated injection regimen, testing occurred within 2-4 hr after each drug administration.

The proportion of animals developing a tumor (i.e., tumor incidence) was analyzed with Fisher Exact Probability tests. Total survival time for all groups of mice inoculated with NB (including those animals that did not develop measurable tumors) was analyzed using a two-tailed Mann-Whitney U test. Time prior to tumor appearance, the time after tumor appearance and the total survival time for tumor-bearing mice only were analyzed using analysis of variance. Body weights were compared with a two-factor analysis of variance. Subsequent planned comparisons were made with the Newman-Keuls test. All analyses were performed using an Apple II Plus computer equipped with a Stats-Plus statistical package.

RESULTS

Within 16 days after tumor cell inoculation, 100% of the mice in the control and 4×0.1 NTX groups had measurable tumors, whereas no mouse in the 0.1 NTX group had a tumor and 55% (5 of 9) of the mice in the 0.4 NTX group had tumors at this time. On day 57 after tumor cell inoculation, when every tumor-bearing mouse in all groups had died, 80% (8 of 10) of the mice in the 0.1 NTX group had not developed a tumor; this proportion was statistically different from both the control and 4×0.1 NTX groups (p 0.001; FIG. 6). Additionally 33% (3 of 9) of the animals in the 0.4 NTX group had not developed tumors by day 57; this proportion was significantly different from controls and the 4×0.1 NTX group (p=0.027, contingency coefficient test). Although the experiment was terminated on day 57, nontumor-bearing mice in the 0.4 NTX and 0.1 NTX groups were observed for 2 additional weeks and no tumors developed.

Mean total survival time, as well as survival time after tumor appearance, of tumor-bearing mice in the 4×0.1 NTX groups were 17% and 26%, respectively, shorter than control values (Table 8). This group also had a significant reduction in mean total survival time with respect to the 0.1 and 0.4 NTX groups. Median total survival time between all four groups, however, appeared comparable. Although mean total survival time in the 0.4 NTX group was significantly longer than controls by 24%, neither time prior to nor time after tumor appearance were significantly altered from control levels but both exhibited a trend towards an increase. Since only 2 animals in the 0.1 NTX group developed tumors, statistical analyses of these values were difficult to interpret. Time prior to tumor appearance was markedly extended in both animals, with these mice surviving for 34 and 46 days after tumor cell inoculation. The range of life expectancy was 19-38 days in the 4×0.1 NTX group in contrast to ranges of 36-57 days and 34-46 days for mice in the 0.4 and 0.1 NTX groups, respectively. Control mice had a range of survival of 28-48 days.

Because only 2 animals in the 0.1 NTX group developed tumors, this group was excluded from statistical analyses insofar as comparisons of tumor size. Evaluation of tumor dimensions in the other groups revealed that on days 6, 9, 12 and 15 following initial tumor appearance, the mean diameter of tumors in the 0.4 and 4×0.1 NTX groups were significantly smaller than control tumors. On days 18, 21, 24, 27 and 30 after tumor appearance, tumor diameters in mice of the 4×0.1 NTX group were comparable to or larger than those of control animals, but tumor diameters were reduced on these days in mice of the 0.4 NTX group. At the time of death, tumor sizes of the 4×0.1 NTX and 0.4 NTX groups were similar to controls (35.0±1.2 mm).

Metastases or lesions were not noted in any group. Body weights of naltrexone and control groups were comparable throughout the experiment.

Figure 7:
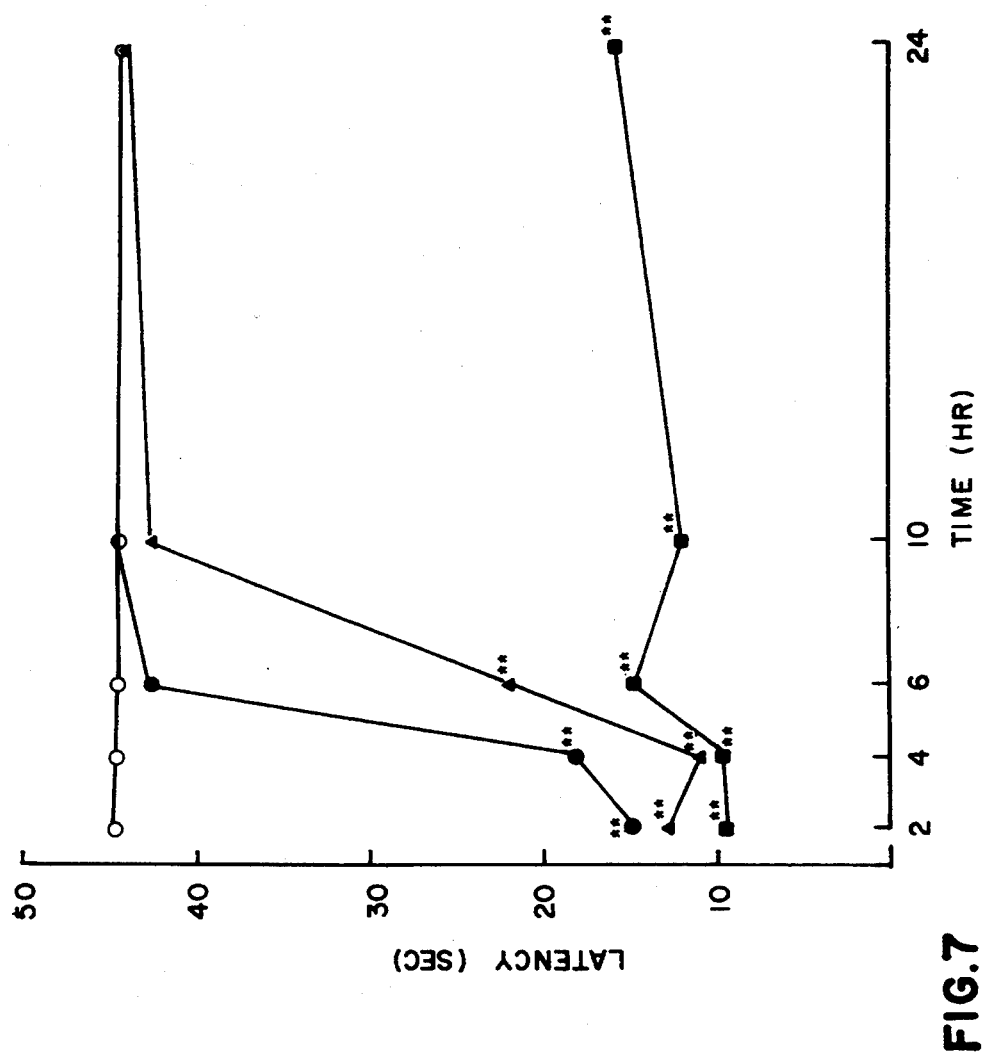
FIG. 7 is a graphic illustration depicting the variance in latency response in mice (challenged with morphine) tested on a hot-plate after subsequent treatment with varying dosages of naltrexone.

As evidenced in opiate challenge experiments (FIG. 7), a dosage of 0.1 NTX invoked an opiate receptor blockade that lasted 4–6 hr, whereas a dosage of 0.4 NTX lasted 6–10 hr. A schedule of 4 daily injections of 0.1 NTX effected an opiate receptor blockade that lasted for the entire 24 hr period.

The results of this study show that low dosages (0.1 mg/kg) of naltrexone administered every 6 hr stimulated tumorigenesis. This finding closely parallels the effects of 10 mg/kg NTX on neuroblastoma recorded in our previous experiments. However, one daily administration of 0.1 mg/kg naltrexone had an antithetical effect (i.e., inhibition of tumorigenicity). In a similar fashion, once daily injections of 0.4 NTX, the sum total of the four times daily injections of 0.1 mg/kg NTX had an antitumor effect. Two of the most prominent differences between treatment schedules of single or repetitive daily administration of NTX were related to tumor incidence and survival time. A 100% tumor incidence occurred in the 4×0.1 NTX group, whereas a 20–33% tumor incidence was found for the 0.1 and 0.4 NTX groups. Secondly, the 4×0.1 NTX group had a mean total survival time that was decreased 19% from control values, whereas a 10–24% increase was recorded in tumor-bearing animals of the 0.1 and 0.4 NTX groups.

EXAMPLE 6

Animals. Adult male and female Sprague-Dawley rats (Charles River Labs, Wilmington, Mass.) were housed under controlled laboratory conditions with water and Agway Lab Chow available ad libitum. Animals were mated and, within 24 hr of birth (day 0), all pups were cross-fostered. Litters were culled to 8 pups per mother, with an equal number of males and females. Beginning on day 1, pups were given daily subcutaneous injections of either naltrexone or an equivalent volume of sterile water (control) until weaning (day 21). Solutions of naltrexone were prepared weekly by dissolving naltrexone (Endo Laboratories, Garden City, N.Y.) in sterile water; dosages are expressed as salts. Rat pups were weighed every two days and appropriate dosage adjustments made.

Dose-Response Experiments. Seven groups of rats (5–14 litters per group) were established and received daily s.c. injections of either 0.1, 1, 10, 20, 50 or 100 mg/kg naltrexone or sterile water. On day 21, a random sampling of 2–3 pups/litter were selected, weighted and sacrificed by cardiac perfusion with 10% neutral buffered formalin. Brains were excised, the olfactory bulbs removed and a transverse cut made at the obex of the fourth ventricle prior to weighing.

Opiate Challenge Experiments. In order to measure the efficacy of naltrexone to block the opiate receptors, 21-day old animals give naltrexone were evaluated for nociceptive response following an injection of morphine. Five groups of 30 animals each were established. Littermates of rats used in the dose-response experiments were injected with either 1, 10, 20 or 50 mg/kg naltrexone or sterile water and randomly selected and given an injection of morphine (0.2 mg/kg) 30 min prior to testing for latency of response (e.g., licking of paws) on a hot-plate (55° C.; Analgesia Meter, Technilabs). Animals were tested only once and they were removed from the hot-plate after 45 sec if no response was observed. Six rats in each group were examined at either 4, 6, 12 or 24 hr following naltrexone injection.

Continuous Versus Intermittent Treatment Regimens. The effect of a single injection of 9 mg/kg naltrexone given once daily from day 1, and a dosage of 3 mg/kg naltrexone given 3 times daily, on body and brain development were evaluated; control rats were injected with sterile water. Eight to 14 animals with an equal number of males and females were employed in each treatment group. At 21 days of age, the animals were weighed, sacrificed by cardiac perfusion, and brain weights monitored according to details given in the dose-response experiments.

Statistical Analyses. Body and brain weights from the dose-response, as well as continuous versus intermittent treatment regimen, experiments were analyzed separately for each experiment using analysis of variance; subsequent comparisons were made with Newman-Keuls tests. In addition, hot-plate latencies were analyzed at each time point using analysis of variance and Newman-Keuls tests. All analyses were performed using an Apple II Plus computer equipped with a Stats-Plus statistical package.

RESULTS

Daily injection of 0.1 to 50 mg/kg naltrexone had no effect on infant viability during the preweaning period. However, daily injections of 100 mg/kg naltrexone resulted in a 40% mortality rate. Interestingly, all of these deaths were recorded with the first week of life and occurred for entire litters.

Naltrexone's effect on body weight (FIG. 8a) was clearly dependent on dosage. Animals receiving 0.1, 1 or 10 mg/kg naltrexone weighed 11.1 to 13.4% less than 21-day old control rats, whereas animals receiving 20, 50 or 100 mg/kg naltrexone weighed 15.8 to 21.5% more than control pups. Comparison of the 0.1, 1 and 10 mg/kg naltrexone groups, as well as the 20, 50 and 100 mg/kg naltrexone groups revealed no between-group difference within either set of dosages.

Figure 8B:
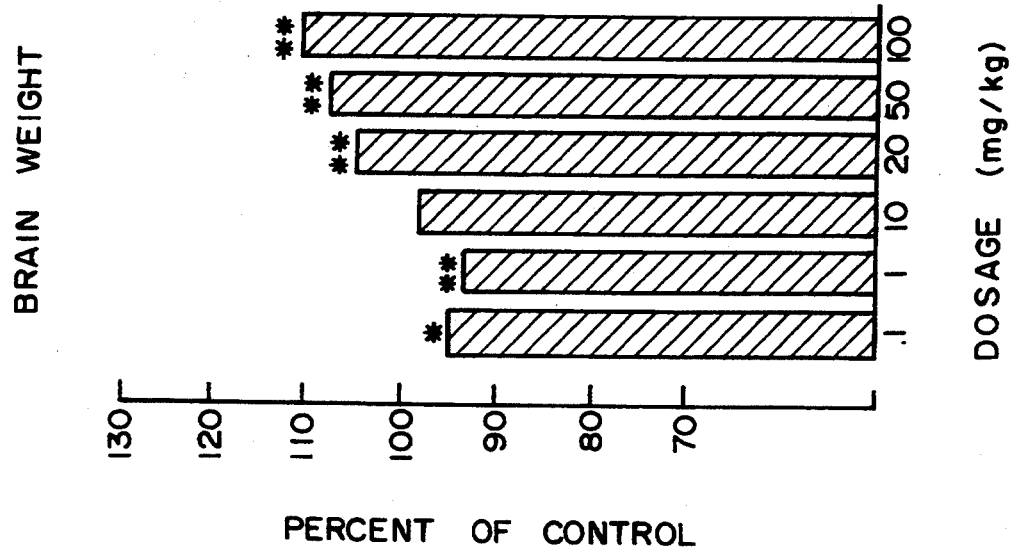
FIG. 8a and FIG. 8b are a set of bar graphs depicting comparative body and brain weights, respectively of preweaning rats receiving treatment with varying dosages of naltrexone.
Figure 8A:
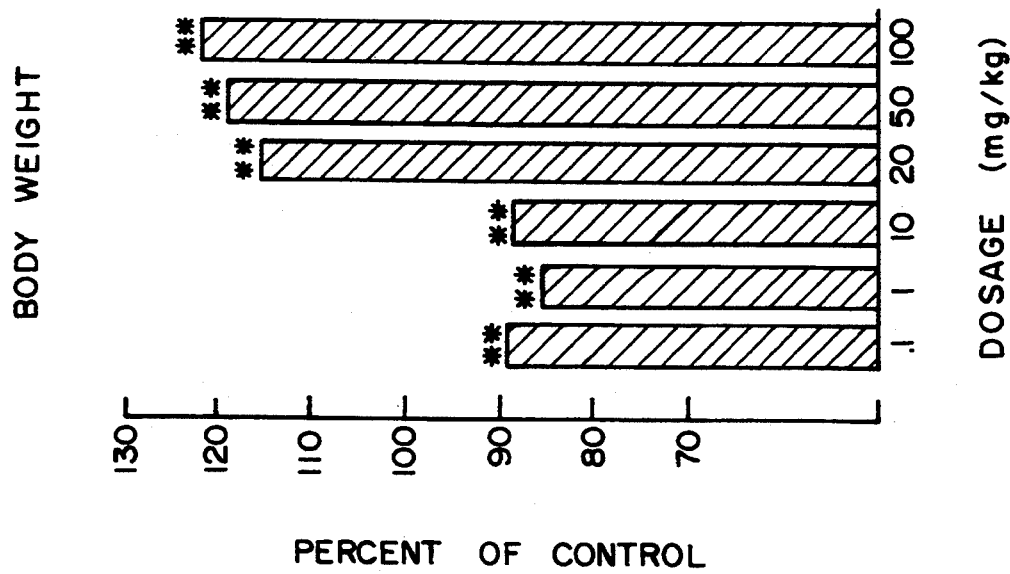

The effects of naltrexone on brain weight were also dependent on dosage (FIG. 8b). Rats in the 0.1 and 1 mg/kg naltrexone groups had brains weighing significantly less (4.6–5.3%) than those of control animals. The brain weights of rats in the 10 mg/kg naltrexone group were also less than control values, but the difference was not statistically significant. Animals in the 20, 50 and 100 mg/kg naltrexone group had brain weights that were increased 6.0–12.6% from control levels.

Figure 9:
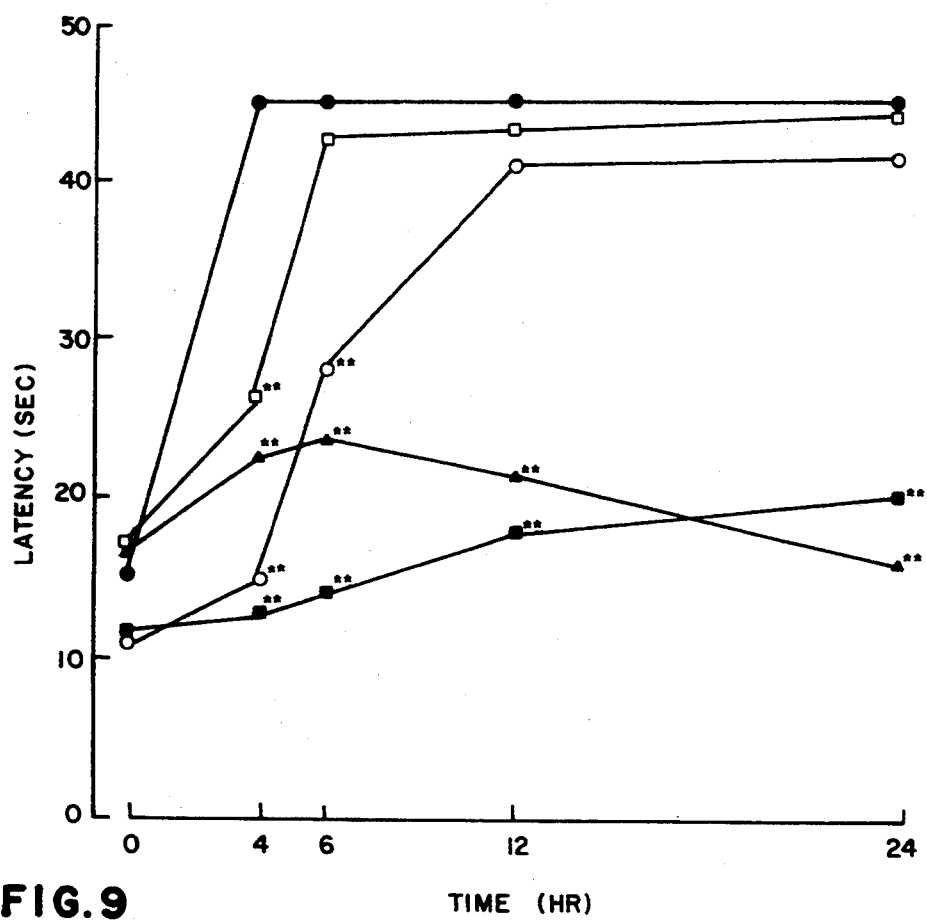
FIG. 9 is a graphic illustration depicting the variance in latency response in young rats (challenged with morphine) tested on a hot-plate after subsequent treatment with varying dosages of naltrexone.

To examine whether the marked biphasic effect of naltrexone was related to naltrexone's pharmacological action on opiate receptor blockade, 21-day old rats receiving either 1, 10 or 50 mg/kg naltrexone were challenged with morphine. The results (FIG. 9) show that a dosage of 1 or 10 mg/kg naltrexone only blocked morphine's antinociceptive effect for 4–6 hr and 6–12 hr, respectively. Dosages of 20 and 50 mg/kg naltrexone exhibited an opiate receptor blockade that lasted for an entire 24 hr period.

Figure 10A:
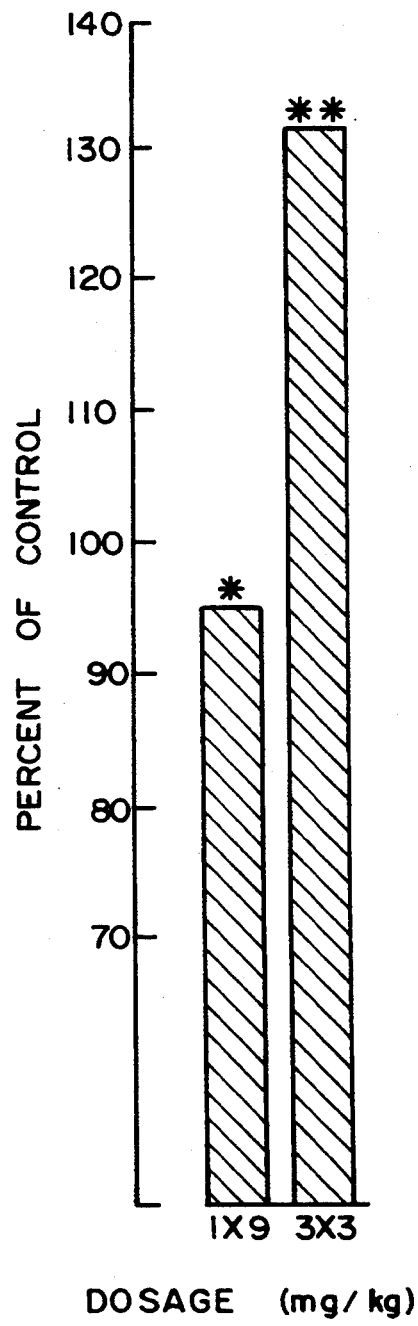
FIG. 10a and FIG. 10b are a set of bar graphs depicting comparative body and brain weights, respectively of young rats receiving treatment with varying dosages of naltrexone.
Figure 10B:
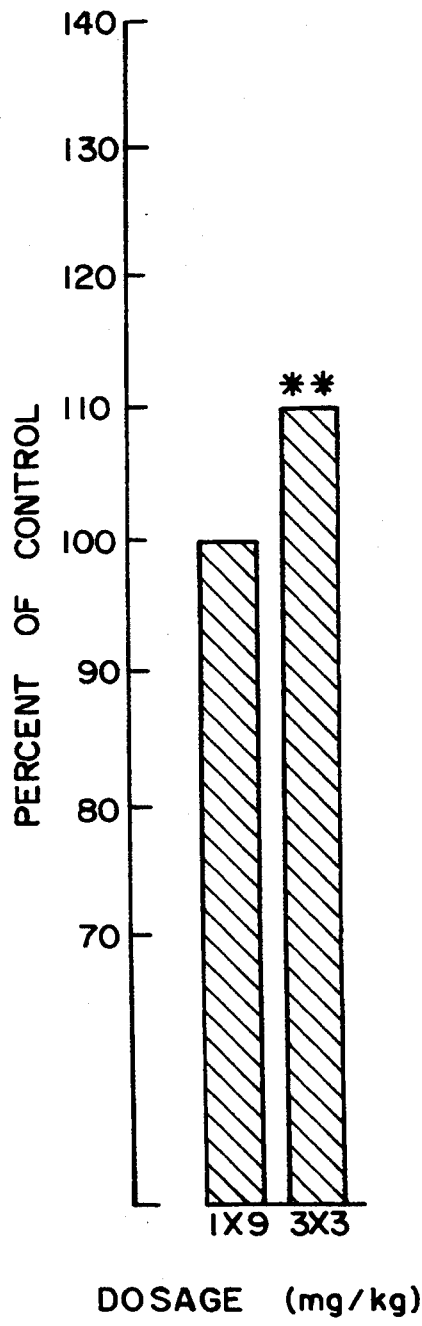

In order to further investigate whether the body and brain development was related to the pharmacological action (to block the opiate receptor) of naltrexone, as well as to explore whether low and high dosages of naltrexone produced growth effects because of interaction with different populations of receptors, another set of experiments was designed. Monitoring measures of growth and nociceptive response as described earlier, we found that rats given 3 mg/kg naltrexone three times daily, which blocked the opiate receptor for an entire 24 hr period, had an increase of 31.1% and 10.2% in body and brain weights, respectively, in comparison to control levels (FIGS. 10a and 10b). However, once daily injections of 9 mg/kg naltrexone, a dosage that only blocked the opiate receptor for 6–12 hr/day, produced a 5.6% decrease in body weight and no statistical change in their brain weight. These results resembled those found earlier for 10 mg/kg naltrexone rats.

A relationship between the dosages of naltrexone utilized in dose-response investigations and their efficacy in blockading the opiate receptors was observed in opiate challenge experiments. Dosages of 10 mg/kg or less blocked the opiate receptors for no longer than 12 hr, whereas dosages of 20–100 mg/kg blocked the opiate receptors for 24 hr. Taken together with the data on growth response, it would appear that a temporary opiate receptor blockade is associated with growth inhibition, whereas a total opiate receptor blockade is related to growth stimulation. That this relationship was more than coincidental was shown in experiments where low dosages of naltrexone given once a day (producing a temporary blockade) resulted in growth inhibition, but low dosages given repetitively each day (producing a total receptor blockade) resulted in growth stimulation. This evidence clearly points to the duration of opiate receptor blockade, rather than drug dosage, as the key element in modulation of growth.

EXAMPLE 7

S20Y Neuroblastoma ($2 \times 10^5$) cells were seeded in a 75 cm$^2$ cultured flask. After 24 hours, four individual cultures were designated by the addition of a) sterile water, b) $10^{-4}$M naltrexone, c) $10^{-6}$M naltrexone and d) $10^{-8}$M naltrexone to the cultures. After 72 hours, the cultures to which $10^{-4}$ naltrexone and $10^{-6}$M naltrexone had been added exhibited between 2 and $3 \times 10^6$ more cells (per unit time) than either the sterile water culture (control) or the culture to which $10^{-8}$M concentration of naltrexone had been added. (See, FIG. 11.)

EXAMPLE 8

A single colony of Pasteurella, multoocida was placed in diluted sterile saline solution and vortexed into suspension. Three individual samples were designated by the inoculation of nutrient broth with aliquots of saline solution, $10^{-4}$M or $10^{-6}$M naltrexone, respectively. The bacterial cultures were incubated for four hours at 37° C. Each bacterial culture was subsequently diluted, plated (calibrated loop) and incubated for 24 hours at 37° C. The number of bacterial colonies was then analyzed and counted. The number of organisms was calculated with a Quebec colony counter after the 24 hour incubation. The mean number of organisms per plate for each group was as follows:

| | |
|---|---|
| saline sample (control) | 157 |
| $10^{-6}$ M naltrexone sample | 362 |
| $10^{-4}$ M naltrexone sample | 535 |

TABLE 1

Organ weights from 21-day old rats treated with naltrexone or sterile water

| Organ | Control (sterile water) | 1 mg/kg Naltrexone | 50 mg/kg Naltrexone |
|---|---|---|---|
| Brain | 1.53 ± .03 | 1.40 ± .01** | 1.65 ± .02** |
| Heart | 0.30 ± .01 | 0.28 ± .01 | 0.36 ± .01** |
| Kidneys | 0.69 ± .02 | 0.58 ± .02** | 0.84 ± .03** |
| Liver | 2.52 ± .12 | 1.97 ± .09** | 3.18 ± .11** |
| Skeletal muscle | 0.25 ± .01 | 0.19 ± .02* | 0.33 ± .02** |

Organ weights represent means (g) ± S.E.M. for 12–18 animals/group, with an equal number of males and females. Data were analyzed using analysis of variance; $p < 0.05$ (*), $p < 0.01$ (**).

TABLE 2

Effects of naltrexone on the appearance of physical parameters and spontaneous motor behavior (walking) in preweaning rats

| Parameter | Median Age (days) | Control (sterile water) | 1 mg/kg Naltrexone | 50 mg/kg Naltrexone |
|---|---|---|---|---|
| Hair covering | 9 | 80% (8–10) | 50% (8–10) | 100% (6–8) |
| Incisor eruption | 9 | 100% (8–9) | 60% (7–9) | 90% (7–9) |
| Ear opening | 10 | 60% (10–12) | 0%* (11–12) | 100% (10–10) |
| Eye opening | 15 | 50% (15–16) | 0%* (16–17) | 100%* (14–15) |
| Walking | 12 | 50% (10–13) | 0%* (13–15) | 100%* (8–12) |

Values represent the proportion of positive response by each treatment group (N = at least 10 rats/group) at the median age of all animals (i.e., the age when 50% of all rats in control and experimental groups demonstrated a positive response). Significantly different from controls at p 0.05 (*). Numbers in parenthesis indicate the range and including the age at which a positive response or characteristic was initially observed for any rat in a given group and the age at which 100% of the animals in each group displayed a positive response.

TABLE 3

Effects of NTX on survival time of mice injected intradermally with NB

| Group | N$^a$ | Survival time Before tumor appearance (mean ± S.E.) | Total Mean ± S.E. | Median | Tumor size (mean ± S.E.)$^d$ |
|---|---|---|---|---|---|
| Control | 13/13 | 11.69 ± 0.48 | 32.54 ± 1.69 | 30 | 25.23 ± 1.90 |
| 0.1 mg/kg NTX | 11/16$^b$ | 19.90 ± 2.50$^c$ | 46.54 ± 1.59$^c$ | 48 | 27.00 ± 1.05 |
| 10.0 mg/kg NTX | 16/16 | 14.20 ± 0.35 | 35.25 ± 1.70 | 36 | 24.33 ± 1.32 |

Survival time (days) of mice injected daily with different concentrations of NTX beginning 2 days after an intradermal inoculation of $10^6$ S20Y NB cells; injections were continued until death. Controls received daily injections of sterile water.
$^a$Proportion of mice with tumors in each group.
$^b$Significantly different from controls at $p < 0.01$ using a chi-square test.
$^c$Significantly different from controls at $p < 0.01$ using analysis of variance. The survival times of only those mice with tumors were analyzed.
$^d$Recorded at death.

TABLE 4

Incidence of metastases in adult mice inoculated with $10^6$ S20Y neuroblastoma cells

| Group | No. mice with tumors | Sites of metastases | | |
|---|---|---|---|---|
| | | Lymph nodes | Lung | Liver |
| Control | 13 | 11 | 4 | 3 |
| 0.1 mg/kg NTX | 11 | 6 | 4 | 0 |
| 10 mg/kg NTX | 16 | 11 | 7 | 9 |

Multiple metastases were infrequently found in the mice so that the total number of metastases may exceed the normal number of mice studied in each group.

TABLE 5

Body, brain and cerebellar measures for 21-day-old rats treated from birth with saline or naltrexone (50 mg/kg). Values are means ± standard errors for 21 to 30 animals per group with an equal number of males and females. Each value for naltrexone-treated animals differs from the corresponding control value at < 0.01 (analysis of variance and Newman-Keuls test).

| Measure | Control group | Naltrexone group |
|---|---|---|
| Body weight (g) | 47.22 ± 0.72 | 55.17 ± 0.91 |
| Brain | | |
| Weight (g) | 1.54 ± 0.02 | 1.71 ± 0.02 |
| Height (mm) | 9.68 ± 0.05 | 10.15 ± 0.05 |
| Length (mm) | 24.32 ± 0.16 | 26.23 ± 0.08 |
| Width (mm) | 15.51 ± 0.06 | 15.88 ± 0.06 |
| Cerebellum | | |
| Weight (mg) | 196.13 ± 3.26 | 210.60 ± 3.45 |
| Width (mm) | 11.12 ± 0.11 | 11.64 ± 0.09 |

TABLE 6

Morphometric analysis of the somatosensory cortex and cerebellum of 21-day-old rats treated from birth with saline or 50 mg/kg naltrexone. Values are means±standard errors for two sections per brain from 12 animals per group (equal numbers of males and females). Coronal sections (8 um) of the somatosensory cortex and midsagittal sections of the cerebellum were stained with hematoxylin and eosin and areas were traced and computed with an Apple Graphics Tablet and Apple II computer. Cerebral width was measured as the distance along a line perpendicular to the midline and extending to the widest portion of the cortex. Cerebral area in each hemisphere encompassed the dorsal limit of layer II of the cortex and the area ventral to the anterior commissure. Cortical widths were measured as perpendicular depths from the dorsal surface of layer II the corpus callosum. Measurements began at the most vertical point of the corpus callosum and proceeded laterally every 8 mm on the tracing until the cerebral width line was reached. Although measurements were made in both hemispheres of each brain there were no differences and thus the data were combined.

| Measure | Control group | Naltrexone group |
|---|---|---|
| Cerebrum | | |
| Width (mm) | 5.06 ± 0.10 | 5.54 ± 0.08* |
| Area (mm$^2$) | 16.12 ± 0.70 | 18.82 ± 0.77+ |
| Cortical thickness (mm) | 1.29 ± 0.04 | 1.52 ± 0.03* |
| Cerebellum | | |
| Total area (mm$^2$) | 12.14 ± 0.60 | 17.15 ± 0.55* |
| Molecular layer area (mm$^2$) | 5.97 ± 0.38 | 8.41 ± 0.34* |
| Internal granule layer area (mm$^2$) | 5.08 ± 0.24 | 7.15 ± 0.27* |
| Medullary layer area (mm$^2$) | 1.08 ± 0.06 | 1.57 ± 0.10* |

*P < 0.01
+P < 0.05

TABLE 7

Cellular content of cerebellar pyramidal lobe sections from 21-day-old rats treated from birth with saline or 50 mg/kg naltrexone. Differential cell counts were made with an ocular grid at X630 magnification with a Nikon Biophot. All cells were counted from the pyramis and the total number of cells per section was computed by multiplying the cell concentration by corresponding areal measurements. In the molecular medullary layers all glial and neuronal cells were counted and endothelial cells were excluded. Only Purkinje cells with distinct nucleoli were counted. At least two sections per cerebellum from 12 animals per group (equal numbers of males and females) were counted. Values are mean numbers of cells±standard errors.

| Cells counted | Control group | Naltrexone group |
|---|---|---|
| Neural cells in molecular layer | 1.527 ± 108 | 4.100 ± 368* |
| Internal granule neurons in internal granule layer | 8.200 ± 615 | 10.623 ± 651* |
| Glial cells in medullary layer | 175 ± 19 | 299 ± 42+ |
| Purkinje cells | 47 ± 3 | 52 ± 2 |

*P < 0.01
+P < 0.05

TABLE 8

| Group | N$^a$ | Survival (days after tumor cell inoculation) | | |
|---|---|---|---|---|
| | | Before tumor appearance Mean ± S.E. | Total Mean ± S.E. | Median |
| Control | 12/12 | 10.0 ± 0.9 | 36.4 ± 1.7 | 36 |
| 4 × 0.1 NTX | 12/12 | 10.7 ± 0.9 | 29.4 ± 2.3$^c$ | 34 |
| 0.4 NTX | 6/9$^b$ | 16.5 ± 5.6 | 45.0 ± 3.8$^c$ | 40 |
| 0.1 NTX | 2/10$^b$ | 19.0 ± 0.0$^c$ | 40.0 ± 5.9 | 34 |

Survival time (days) of mice injected with different concentrations of NTX beginning 2 days after a subcutaneous inoculation of $10^6$ S20Y NB cells; injections were continued until death. Controls received daily injections of sterile water.
$^a$Proportion of mice with tumors in each group.
$^b$Significantly different from control and 4 × 0.1 NTX groups at p < 0.05.
$^c$Significantly different from controls at p < 0.05 using ANOVA.

TABLE 9

Brain weights of 1 mg/kg naltrexone rats and control animals matched for body weight

| | 1 mg/kg naltrexone | Control-matched (to 1 mg/kg naltrexone) |
|---|---|---|
| Body weight (g) | 42.22 ± 2.80 | 41.98 ± 2.98 |
| Brain weight (g) | 1.35 ± 0.04* | 1.42 ± 0.06 |

Values represent means ± SD for at least 10 rats/group.
*Significantly different from control-matched weights at p < 0.01; data were analyzed using analysis of variance.

Thus, while the invention has been described with reference to certain preferred embodiments, those skilled in the art will realize that changes and modifications may be made thereto without departing from the full and intended scope of the appended claims.

What is claimed is:

1. A method for the treatment and alleviation of pain and addictive behavior in a human subject comprising the administration of at least one opioid antagonist to effect temporary blockade of the opioid receptor site in said subject by administering said at least one opioid antagonist in a cumulative amount of less than about 10 mg per day.

2. The method of claim 1 wherein said at least one antagonist is selected from the group consisting essentially of naloxone, naltrexone, their derivatives, analogs, metabolites and mixtures thereof.

* * * * *